United States Patent
Rettig, Jr.

(10) Patent No.: US 12,179,058 B2
(45) Date of Patent: *Dec. 31, 2024

(54) INCENTIVE SPIROMETER FOR SUSTAINED MAXIMAL INSPIRATION

(71) Applicant: David L. Rettig, Jr., Weatherford, TX (US)

(72) Inventor: David L. Rettig, Jr., Weatherford, TX (US)

(*) Notice: Subject to any disclaimer, the term of this patent is extended or adjusted under 35 U.S.C. 154(b) by 1341 days.

This patent is subject to a terminal disclaimer.

(21) Appl. No.: 16/436,323

(22) Filed: Jun. 10, 2019

(65) Prior Publication Data

US 2019/0290960 A1 Sep. 26, 2019

Related U.S. Application Data

(63) Continuation-in-part of application No. 16/361,656, filed on Mar. 22, 2019, now abandoned, which is a continuation of application No. 14/304,923, filed on Jun. 14, 2014, now Pat. No. 10,238,914.

(60) Provisional application No. 61/835,026, filed on Jun. 14, 2013.

(51) Int. Cl.
*A63B 23/18* (2006.01)
*A61B 5/08* (2006.01)
*A61B 5/087* (2006.01)

(52) U.S. Cl.
CPC ............... *A63B 23/18* (2013.01); *A61B 5/08* (2013.01); *A61B 5/0875* (2013.01)

(58) Field of Classification Search
CPC . A63B 23/18; A63B 21/0088; A63B 71/0622; A63B 71/0669; A63B 2071/0625; A63B 2071/0694; A63B 2225/09; A63B 2225/74; A61B 5/08; A61B 5/0875
See application file for complete search history.

(56) References Cited

U.S. PATENT DOCUMENTS

| | | | |
|---|---|---|---|
| 3,889,660 A | 6/1975 | Kitrilakis | |
| 4,079,937 A * | 3/1978 | Kirsch | A63F 9/001 273/119 B |
| 4,094,508 A | 6/1978 | Kirsch | |

(Continued)

FOREIGN PATENT DOCUMENTS

| | | |
|---|---|---|
| WO | WO199836687 A1 | 8/1998 |
| WO | WO2011018788 A1 | 2/2011 |
| WO | WO2015192116 A1 | 12/2015 |

OTHER PUBLICATIONS

International Search Report and Written Opinion, PCT/US2015/035717, dated Nov. 12, 2015.

*Primary Examiner* — Andrey Shostak
(74) *Attorney, Agent, or Firm* — Law Office of Sam Sokhansanj PLLC

(57) ABSTRACT

An incentive spirometer is disclosed having a helical tube, wherein the helical tube includes a first inlet, second outlet, third outlet, and fourth outlet. The spirometer further includes a chamber, wherein the chamber is in fluid communication with the first inlet, second outlet, third outlet, and fourth outlet of the helical tube; and an object disposed within the spirometer, wherein the object is adapted to move through the first inlet of the helical tube and through either the second outlet, third outlet, or fourth outlet. In addition, the spirometer further includes an inhalation draw tube in fluid communication with the chamber and helical tube.

19 Claims, 17 Drawing Sheets

(56) References Cited

U.S. PATENT DOCUMENTS

| | | | | |
|---|---|---|---|---|
| 4,114,607 | A | * | 9/1978 | Russo .................... A63B 23/18 |
| | | | | 482/13 |
| 4,232,683 | A | | 11/1980 | Bartholomew et al. |
| 4,324,260 | A | | 4/1982 | Puderbaugh |
| 4,391,283 | A | | 7/1983 | Sharpless et al. |
| 4,441,239 | A | * | 4/1984 | Mullen ................ B23P 15/003 |
| | | | | 29/898.061 |
| 4,533,137 | A | | 8/1985 | Sonne |
| 4,955,840 | A | | 9/1990 | Moomaw |
| 5,603,314 | A | * | 2/1997 | Bono .................... A61M 11/06 |
| | | | | 128/205.12 |
| 5,829,751 | A | | 11/1998 | Willis |
| 6,238,353 | B1 | | 5/2001 | Weinstein et al. |
| 8,245,705 | B2 | | 8/2012 | Li |
| 2007/0089740 | A1 | * | 4/2007 | Baumert ........... A61M 16/0488 |
| | | | | 128/200.24 |
| 2013/0303930 | A1 | | 11/2013 | Elefteriades et al. |

\* cited by examiner

INCENTIVE SPIROMETER FOR SUSTAINED MAXIMAL INSPIRATION

CROSS REFERENCE TO RELATED APPLICATIONS

This application is a continuation-in-part of U.S. Non-Provisional application Ser. No. 16/361,656 filed on Mar. 22, 2019, which is incorporated herein by reference in its entirety, which is a continuation of U.S. Non-Provisional application Ser. No. 14/304,923 filed on Jun. 14, 2014, which is incorporated herein by reference in its entirety, which claims the benefit of U.S. Provisional Application No. 61/835,026 filed on Jun. 14, 2013, which is incorporated herein by reference in its entirety.

BACKGROUND

This section is intended to introduce the reader to aspects of art that may be related to various aspects of the disclosure described herein, which are described and/or claimed below. This discussion is believed to be helpful in providing the reader with background information to facilitate a better understanding of the various aspects of the disclosure described herein. Accordingly, it should be understood that these statements are to be read in this light, and not as admissions of prior art.

Incentive spirometers have been developed in order to help correct and prevent inadequate ventilation and collapsed alveoli due primarily to the shallow pattern of breathing following surgery. These devices have been designed to encourage patients to breathe when they might otherwise suppress their normal breathing from reasons such as pain from their surgical incisions, under-utilization of the lungs, chronic respiratory conditions such as cystic fibrosis, or from prolonged periods of lying in bed. If the technique is properly explained and taught to the patient, then the incentive spirometer will allow the patient to perform breathing exercises on his or her own time. The basic idea is to encourage the patient to make a prolonged inspiratory effort, which he or she might otherwise suppress.

Currently, incentive spirometers on the market generally have an indicator that provides a gauge of how well the patient's lung or lungs are functioning, by indicating an approximate tidal or lung volume inspired with each breath. The patient is generally asked to perform many repetitions a day while measuring his or her progress by way of the gauge. However, this type of indicator does not differentiate between a desired Sustained Maximal Inspiration (SMI) or a rapid inspiratory burst (or cheat), nor does it provide adequate motivation for certain patients, such as pediatric patients, to continue using the spirometer. Hence, improper, infrequent or sporadic use of the spirometer could thereby prolong the patient's lung recovery, thereby possibly resulting in prolonged hospital stays or even relapse.

Thus, a spirometer capable of stimulating the user's curiosity, playfulness, and motivation, and desired Sustained Maximal Inspiration (SMI) while aiding the development of lung capacity and respiratory musculature is desired.

BRIEF SUMMARY

In one aspect of the disclosure described herein, an incentive spirometer device is disclosed that is capable of holding the user's attention and motivating the user to continue its use, while recruiting collapsed alveoli, and strengthening the muscles of the user's respiratory system through repetitive Sustained Maximal Inspiration's (SMI). Further, the spirometer of the disclosure described herein is simple to operate by either pediatric or adult users, visually appealing, and is cost effective to manufacture in large quantities.

In particular, in one aspect of the disclosure described herein, a method and apparatus are provided for a three-dimensional incentive spirometer having a plurality of chambers, wherein each chamber includes a ball traveling upwards through a helical tube and subsequently dropping down through a basket. Here, each of the helical tubes and corresponding baskets generally represent various levels of lung capacity achieved with repetitive use and operation of the spirometer.

In another aspect of the disclosure described herein, a spirometer is provided having an air tube, a chamber, and a helical tube, wherein the helical tube is in fluid communication with the air tube and the chamber. In addition, an object disposed within the helical tube, wherein the spirometer is configured to allow the object to move through the helical tube in response to inhalation or low pressure. The spirometer can further include a reciprocating gate adjacent to an outlet of the helical tube and wherein the reciprocating gate is coupled to a push down button. Here, the push down button is configured to align an aperture of the reciprocating gate with an outlet of the helical tube. Also, the object can be a spherical ball and the chamber can include one or more basketball hoops. The spirometer can further include a second helical tube and a second chamber, wherein the second chamber is in fluid communication with the air tube and second helical tube. In addition, the spirometer can also include a third helical tube and a third chamber, wherein the third chamber is in fluid communication with the air tube and third helical tube.

In another aspect of the disclosure described herein, a method of operation for a spirometer is provided. The method can include from a drawtube, wherein the drawtube is coupled to an air tube, and wherein the air tube is coupled to a helical tube. The method can further include building low pressure within the air tube and the helical tube through the inhalation, wherein the low pressure causes an object to travel through the helical tube, and actuating a button to operate a gate adjacent to an outlet of the helical tube, wherein the object exits the helical tube upon actuation of the button.

In another aspect of the disclosure described herein, a method of operating an incentive spirometer is provided. The method can include inhaling through a drawtube of the spirometer, wherein the inhalation creates low pressure within a helical tube of the spirometer, thereby causing an object to travel through the tube, wherein the spirometer is configured to achieve sustained maximal inspiration.

In another aspect of the disclosure described herein, an incentive spirometer is disclosed having a helical tube, wherein the helical tube comprises a first inlet, second outlet, third outlet, and fourth outlet. The spirometer further includes a chamber, wherein the chamber is in fluid communication with the first inlet, second outlet, third outlet, and fourth outlet of the helical tube; and an object disposed within the spirometer, wherein the object is adapted to move through the first inlet of the helical tube and through either the second outlet, third outlet, or fourth outlet. In addition, the spirometer further includes a housing having a first half and second half secured together. In addition, the spirometer further includes a draw tube in fluid communication with the chamber and helical tube. In addition, the spirometer also includes an adjustable air valve configured to adjust inhalation pressure within the spirometer or air flow through the spirometer and helical tube. The spirometer also includes a receiving member configured to receive the object therein, wherein the receiving member is disposed within the chamber. In addition, the receiving member is comprised of a basket. The spirometer further includes movable gate or plate disposed below the receiving member, wherein the receiving member further includes an opening therein. In addition, the gate is configured to slide thereby releasing the object disposed within the receiving member.

The above summary is not intended to describe each and every disclosed embodiment or every implementation of the disclosure. The Description that follows more particularly exemplifies the various illustrative embodiments

BRIEF DESCRIPTION OF THE DRAWINGS

The following description should be read with reference to the drawings, in which like elements in different drawings are numbered in like fashion. The drawings, which are not necessarily to scale, depict selected embodiments and are not intended to limit the scope of the disclosure. The disclosure may be more completely understood in consideration of the following detailed description of various embodiments in connection with the accompanying drawings, in which.

DETAILED DESCRIPTION

Figure 1:
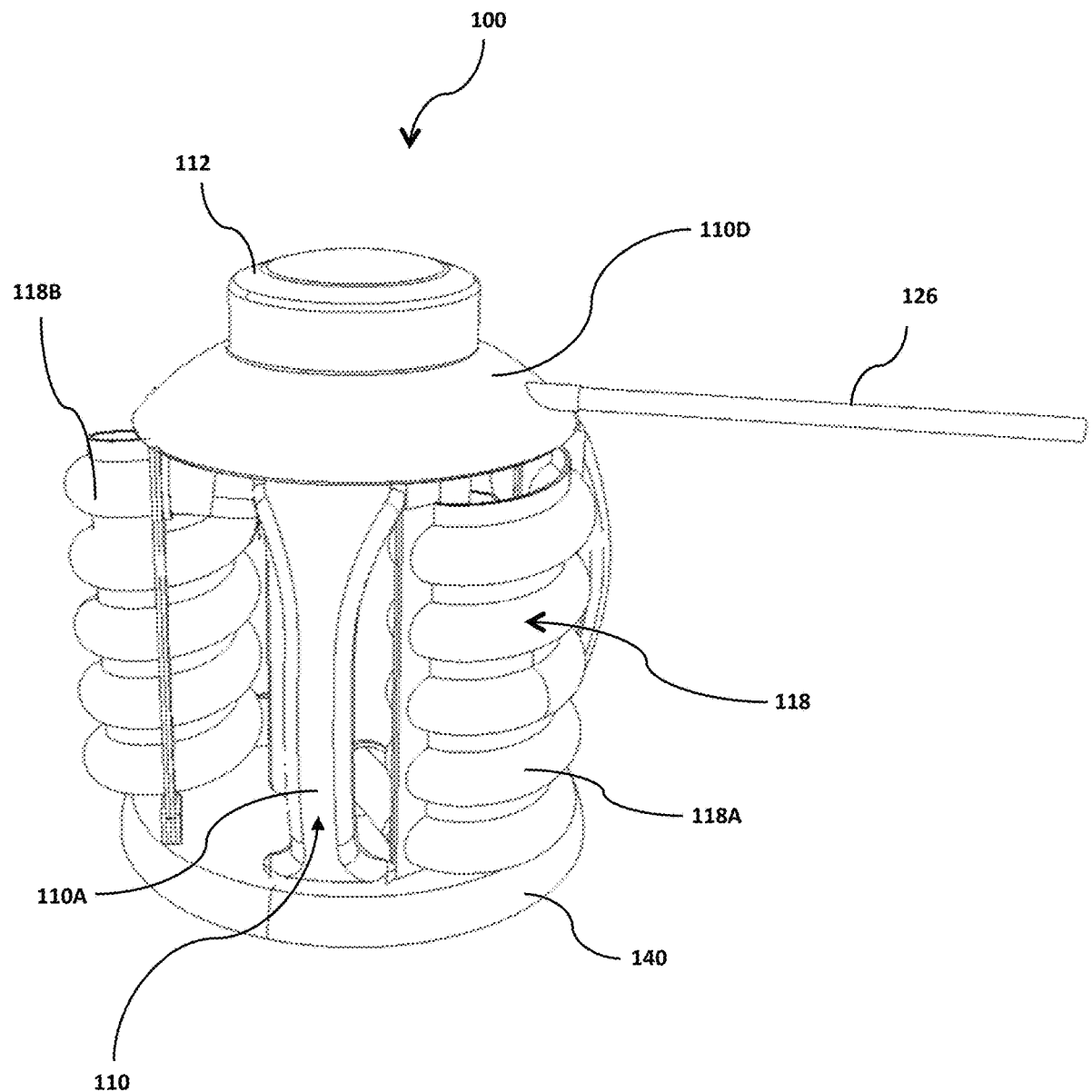
FIG. 1 illustrates a perspective view of the incentive spirometer as fully assembled according to one non-limiting embodiment of the disclosure described herein.
Figure 2:
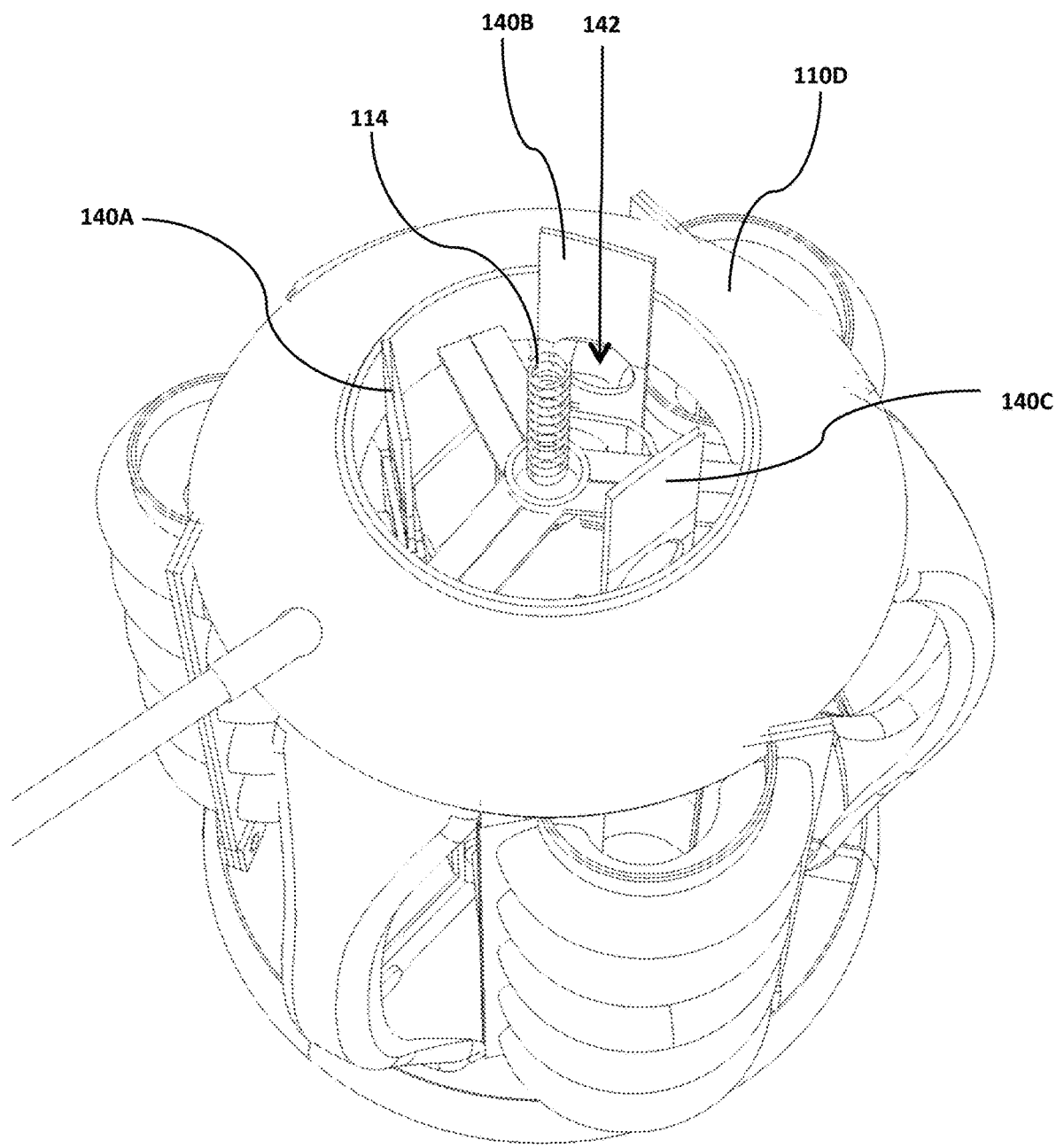
FIG. 2 illustrates a perspective top view with the push down release button removed.
Figure 3:
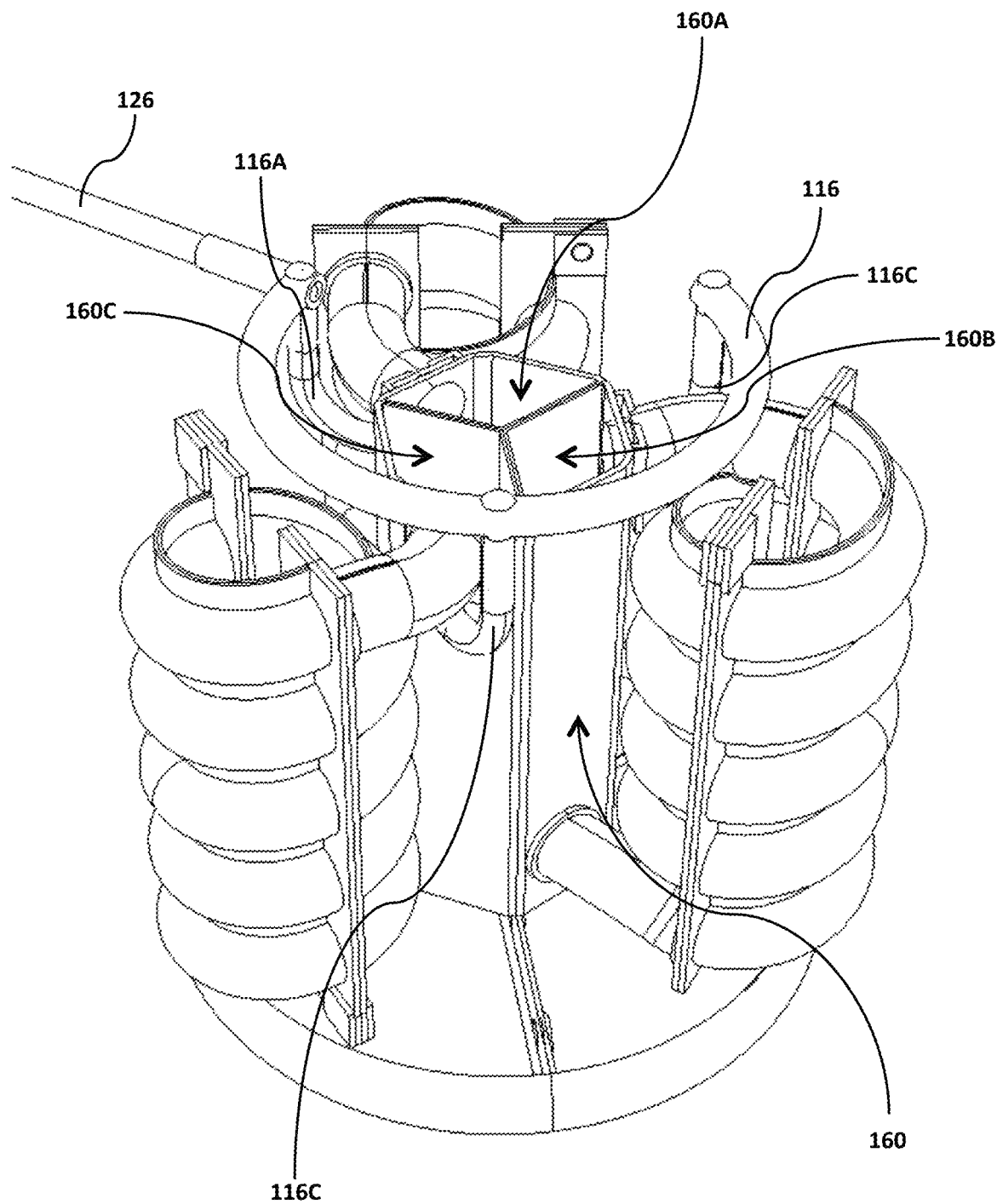
FIG. 3 illustrates a perspective top view of the incentive spirometer with the top bezel cover and push down button removed.
Figure 4:
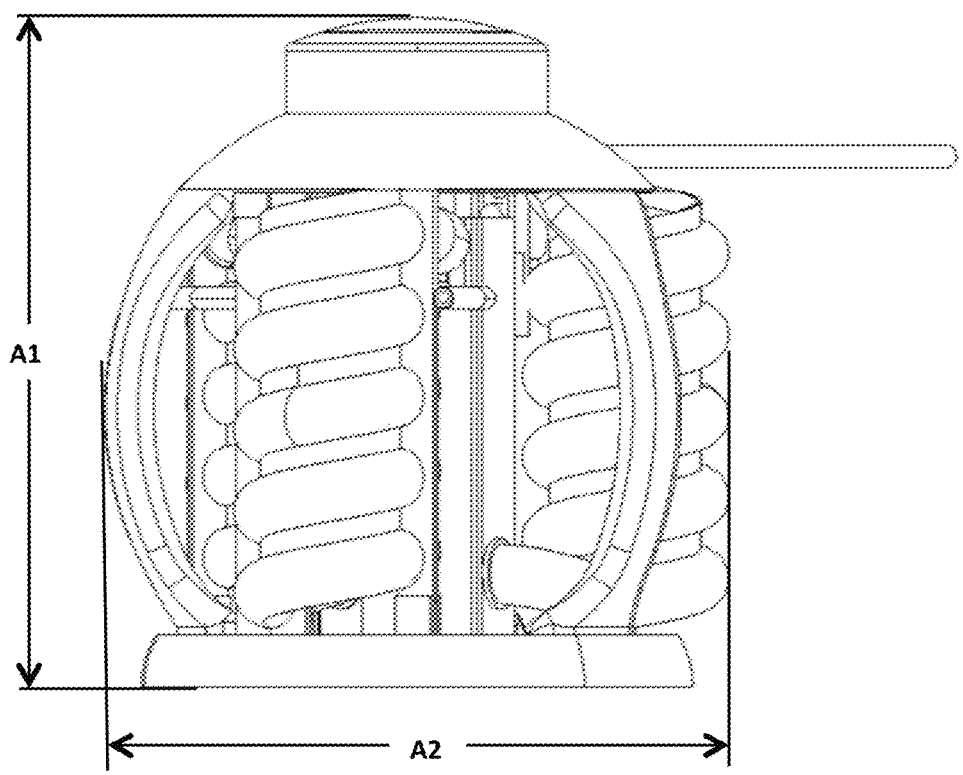
FIG. 4 illustrates a side view of the incentive spirometer as fully assembled.
Figure 5:
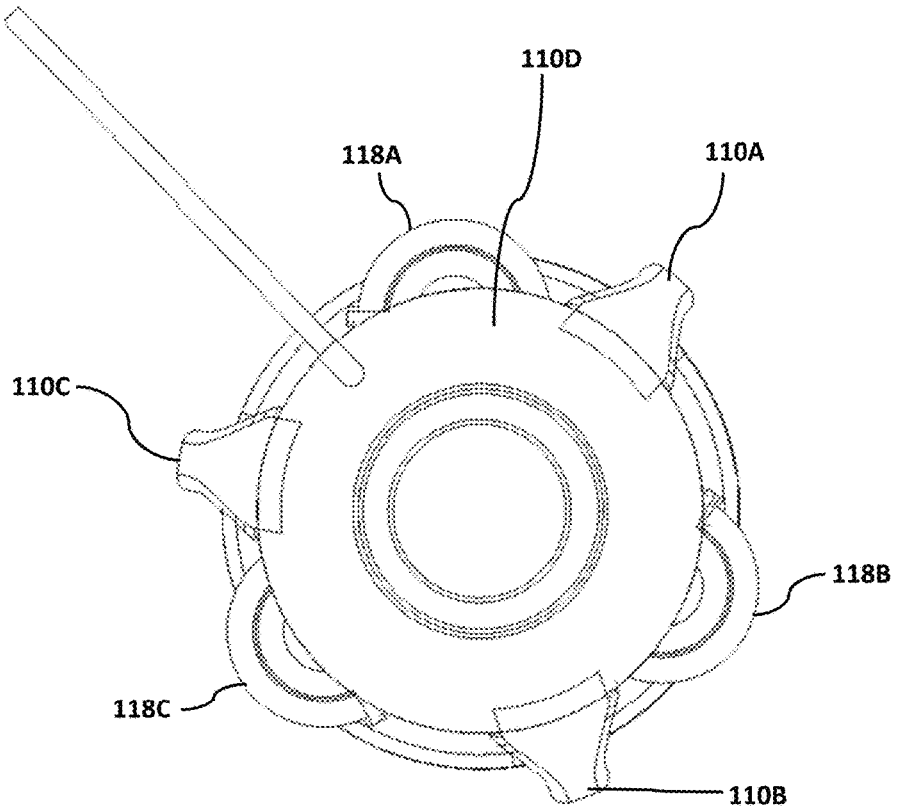
FIG. 5 illustrates a top view of the incentive spirometer as fully assembled.

In the Summary above and in the Detailed Description, and the claims below, and in the accompanying drawings, reference is made to particular features (including method steps) of the disclosure described herein. It is to be understood that the disclosure of the disclosure described herein in this specification includes all possible combinations of such particular features. For example, where a particular feature is disclosed in the context of a particular aspect or embodiment of the disclosure described herein, or a particular claim, that feature can also be used, to the extent possible, in combination with and/or in the context of other particular aspects and embodiments of the disclosure described herein, and in the disclosure described herein generally. The term "comprises" and grammatical equivalents thereof are used herein to mean that other components, ingredients, steps, etc. are optionally present. For example, an article "comprising" (or "which comprises") components A, B, and C can consist of (i.e., contain only) components A, B, and C, or can contain not only components A, B, and C but also one or more other components. Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range beginning with that number (which may be a range having an upper limit or no upper limit, depending on the variable being defined). For example "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)-(a second number)," this means a range whose lower limit is the first number and whose upper limit is the second number. For example, 25 to 100 mm means a range whose lower limit is 25 mm, and whose upper limit is 100 mm. The embodiments set forth below represent the necessary information to enable those skilled in the art to practice the disclosure described herein and illustrate the best mode of practicing the disclosure described herein. In addition, the disclosure described herein does not require that all the advantageous features and all the advantages need to be incorporated into every embodiment of the disclosure described herein.

The embodiments set forth below represent the necessary information to enable those skilled in the art to practice the disclosure described herein and illustrate the best mode of practicing the disclosure described herein. In addition, the disclosure described herein does not require that all the advantageous features and all the advantages need to be incorporated into every embodiment of the disclosure described herein.

Figure 10:
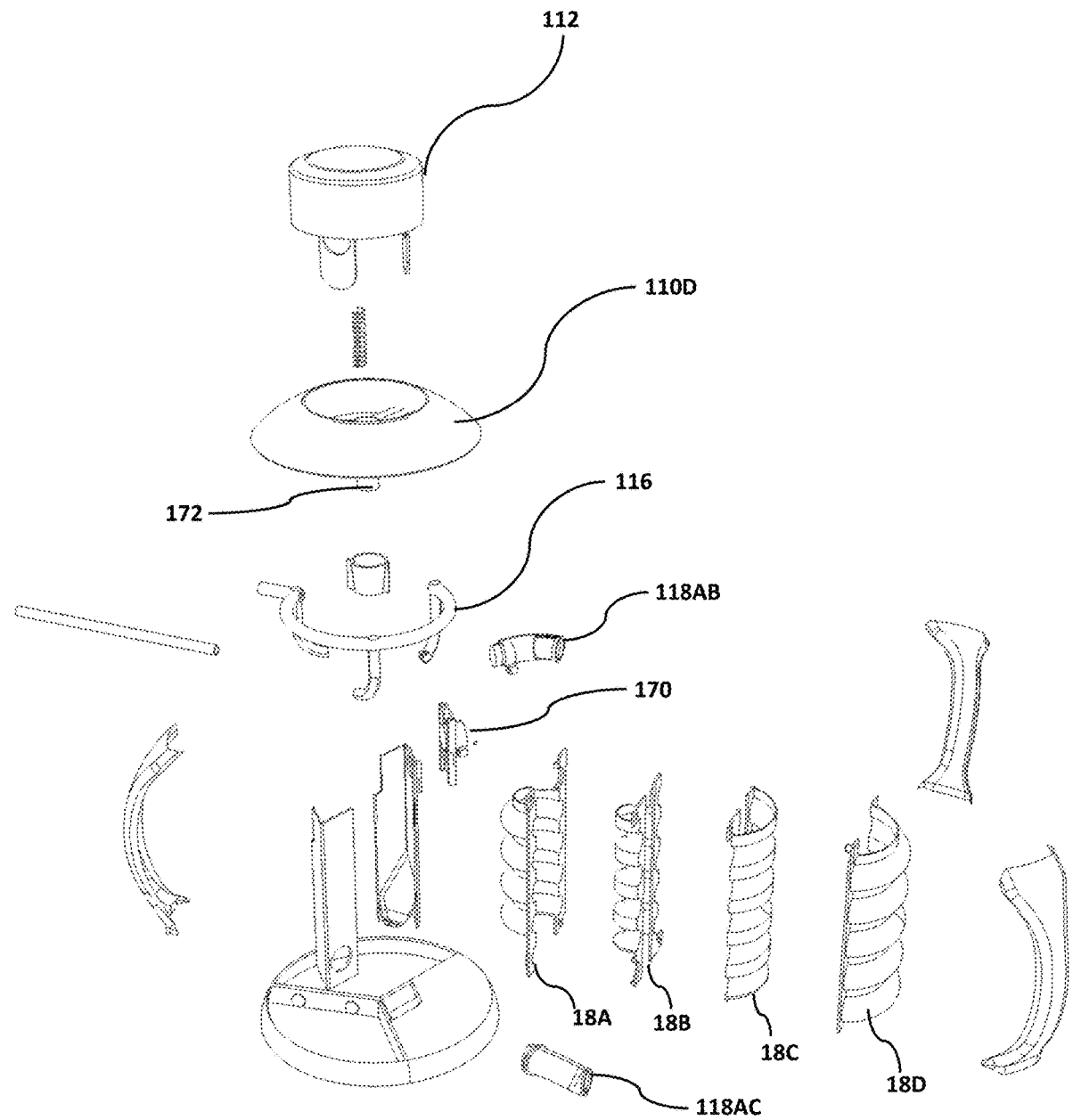
FIG. 10 illustrates an exploded view of the incentive spirometer, illustrating one of the helical tubes and related components, wherein the other two helical tubes are omitted for illustration purposes.
Figure 11:
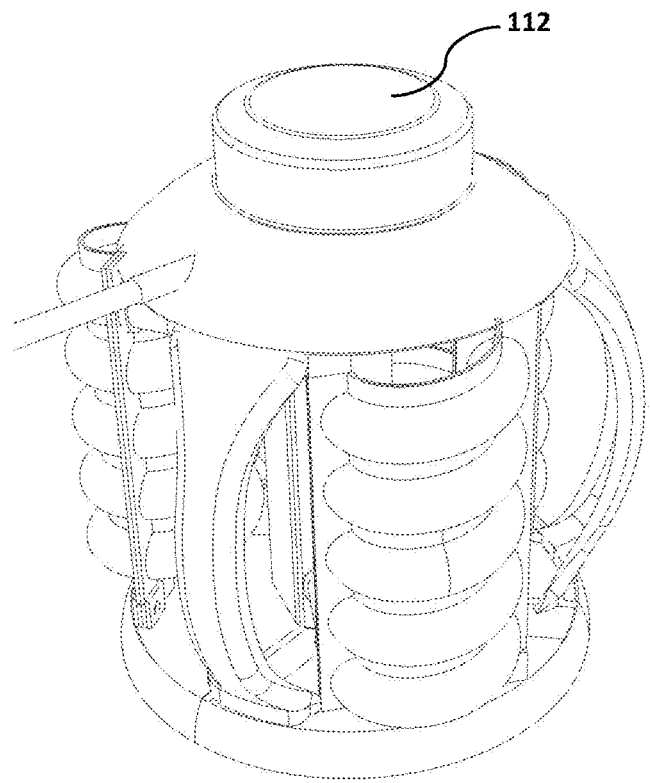
FIGS. 11-12 illustrate perspective views of the incentive spirometer as fully assembled, illustrating a method of depressing the push down button.

Referring now to FIGS. 1-6 of the drawings, one embodiment for the incentive spirometer 100 of the disclosure described herein can include a shell, casing, housing, or frame 110 having a generally spherical, oval, or ball shaped configuration. Frame 110 further includes a top bezel housing cover 110D connected to support pillars or arms 110A, 110B, and 110C. In addition, frame 110 further includes a bottom support or plate 140 connected to arms 110A-110C. Top bezel housing cover 110D further includes an aperture that at least partially encloses or encircles push down pressure release button 112 coupled to compression spring 114, wherein button 112 is further coupled to sliding gates 140A, 140B, and 140C. Here, each of gates 140A-140C are supported by a bracket or guide 170 (FIG. 10), wherein gates 140A-140C can slide therein. In addition, spirometer 100 includes spiral or helical tubes 118, and more specifically, helical or spiral tubes 118A, 118B, and 118C, wherein spirals tubes 118A-118C are tubular and hollow in configuration. Here, spiral tubes 118A-118C each include at least one object or spherical ball that travels upwards through the interior helical configuration of tubes 118A-118C. Here, the spherical ball can be approximately 1-6 grams in weight. The dimensions of spirometer can be anywhere from 4 in.×4 in.×4 in. up to and including 12 in.×12 in. and 12 in. For example, referring to FIGS. 4, A1 and A2 can be anywhere from approximately 4 inches up to and including 12 inches. Further, spiral tubes 118A, 118B, and 118C can each have a height or length of approximately 6 to 10 inches, and a width of approximately 1 to 4 inches. In addition, spirals 118A, 118B, and 118C can each have an inner diameter of approximately 0.25 to 2.0 inches and outer diameter of approximately 0.75 to 4.5 inches. Here, the outer diameter can be approximately 2-3 times the size of the inner diameter. Each of tubes 118A-118C can be manufactured and assembled in four parts 18A-18D (see FIG. 10), wherein parts 18A and 18D form the outer walls and parts 18B and 18C form the inner walls, and wherein all parts 18A-18D can be joined together via heated fusion, adhesives, bolts, screws, or snap-fit, among others.

Still referring to FIGS. 1-6, spirometer 100 further includes upstanding column 160 having three divided chambers or air spaces, namely chambers 160A, 160B, and 160C, wherein each chamber is separated by a several partitions or walls. Here, each chamber includes a fixed basket (i.e. basketball scoring basket) namely baskets 122A, 122B, and 122C wherein each basket is offset or placed at different heights with respect to each other. Here, the baskets prowvide a visual effect as each ball from each spiral tube fall therethrough upon the release of pressure by the action of a user pressing down button 112, which will be described in detail later. In the current embodiment, baskets 122A-122C resemble traditional netted basketball baskets or hoops. However, it is contemplated within the scope of the disclosure described herein that the baskets can be any type of sports goal, basket, or visual indicator for scoring may be used. In other embodiments, the spirometer may have no baskets. In addition, as illustrated in FIG. 7-8B, each of chambers 160A-160B include a floor 124 having a curved dome or an offset/angled ramp with respect to a horizontal plane. Here, the angled floor 124 allows a ball within each chamber 160A-160C to naturally navigate towards the inlets 128 for each of tubes 118A-118C.

Figure 9A:
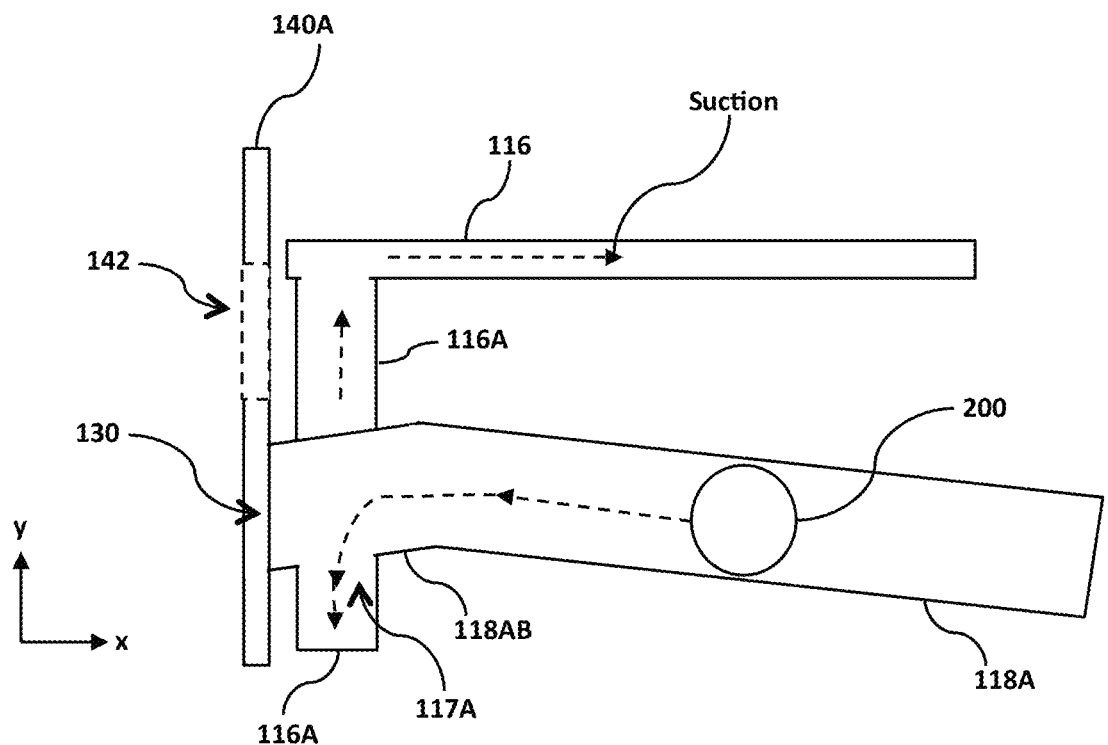
FIG. 9A-9B illustrates a close-up cross-sectional side view of the incentive spirometer, illustrating one of the spirals, top circular tube, and gate, further illustrating the method of operation, according to one non-limiting embodiment of the disclosure described herein.
Figure 9B:
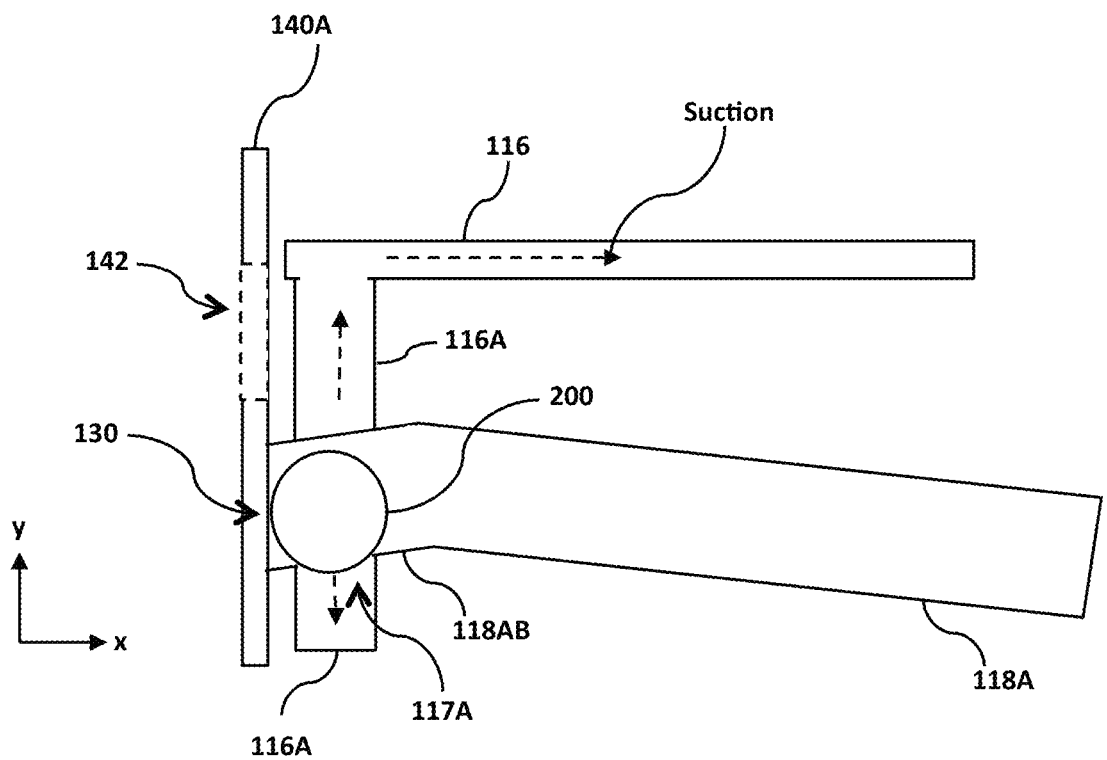

Still referring to FIGS. 1-7, an inhalation tube or drawtube 126 is attached to a horizontal circular air tube 116. Air tube 116 includes a plurality of ports or U-shaped connectors 116A, 116B, and 116C that connect to an air hole, port, or aperture on a bottom surface of each of spiral tubes 118A, 118B, and 118C near outlet 130, respectively, as shown in FIGS. 9A-9B. Here, drawtube 126 and air tube 116 are in fluid communication with each of helical tubes 118A-118C via connectors 116A-116C, and tubes 118A-118C are in further fluid communication with each of chambers 160A-160B, respectively.

Figure 7:
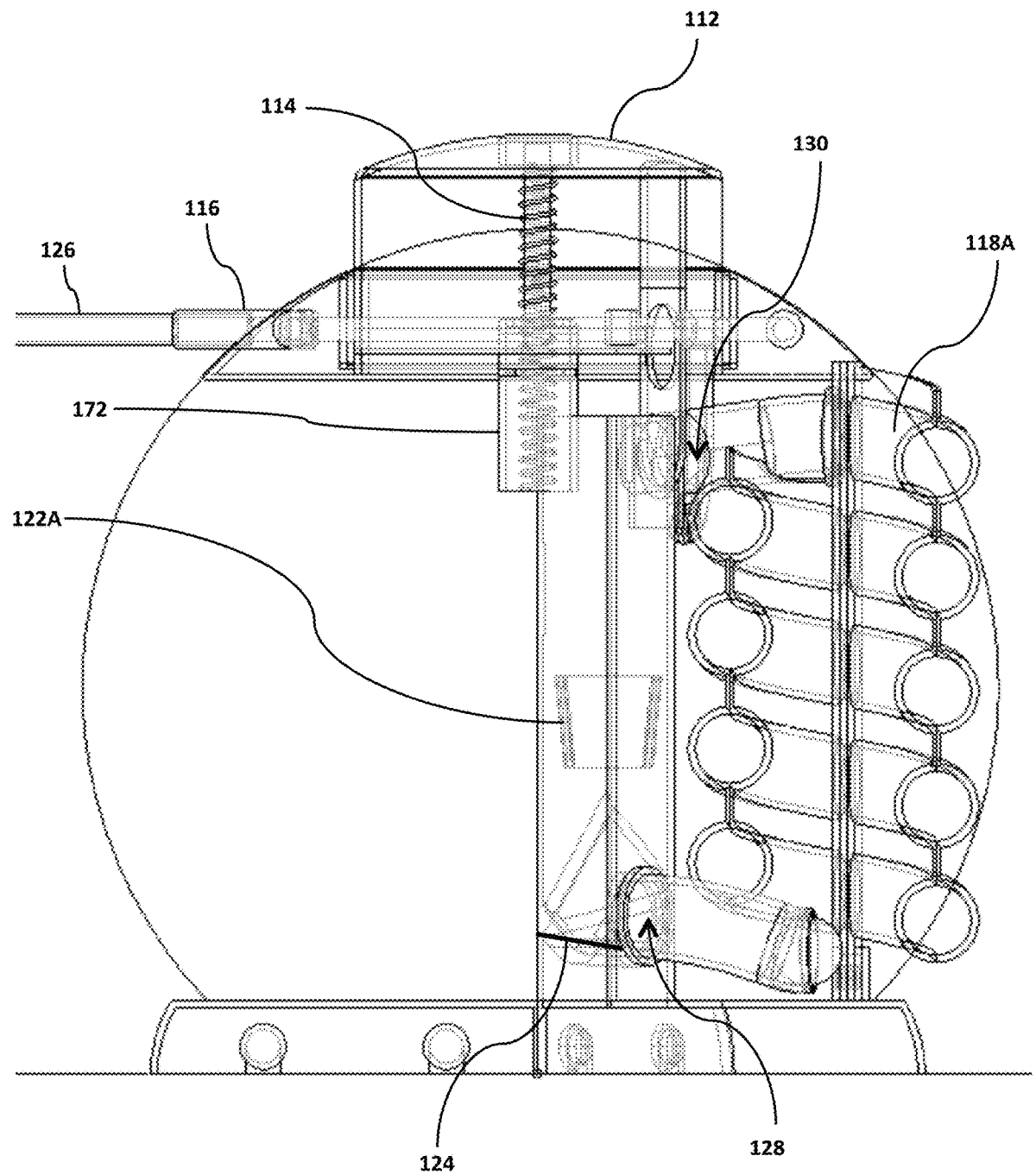
FIG. 7 illustrates a cross-sectional side view of the incentive spirometer, illustrating one of the helical tubes and other components, wherein the other two helical tubes are omitted for illustration purposes.
Figure 8A:
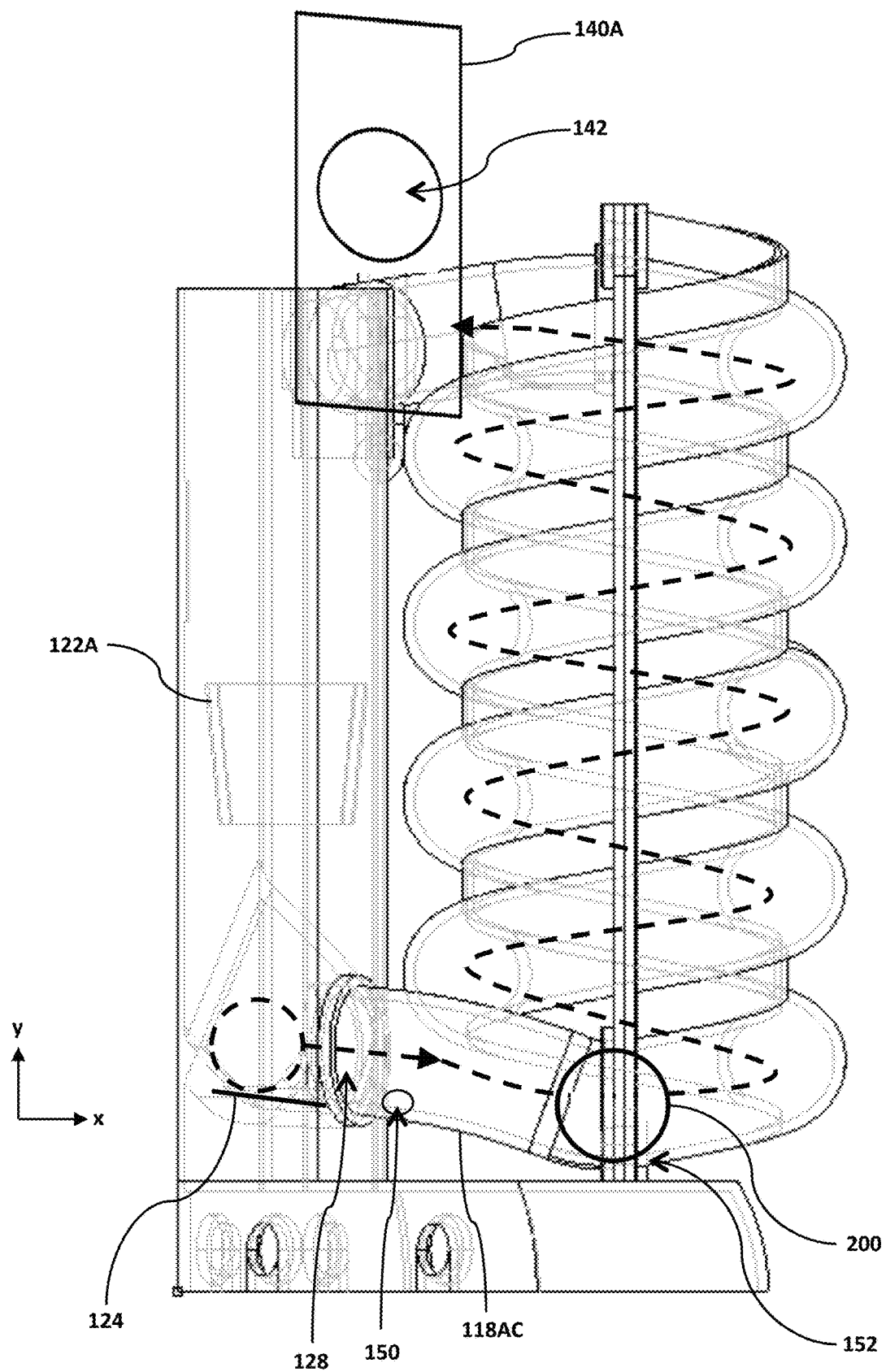
FIG. 8A-8B illustrates a close-up cross-sectional side view of the incentive spirometer, illustrating one of the helical tubes and other components, further illustrating a method of operation, according to one non-limiting embodiment of the disclosure described herein.
Figure 8B:
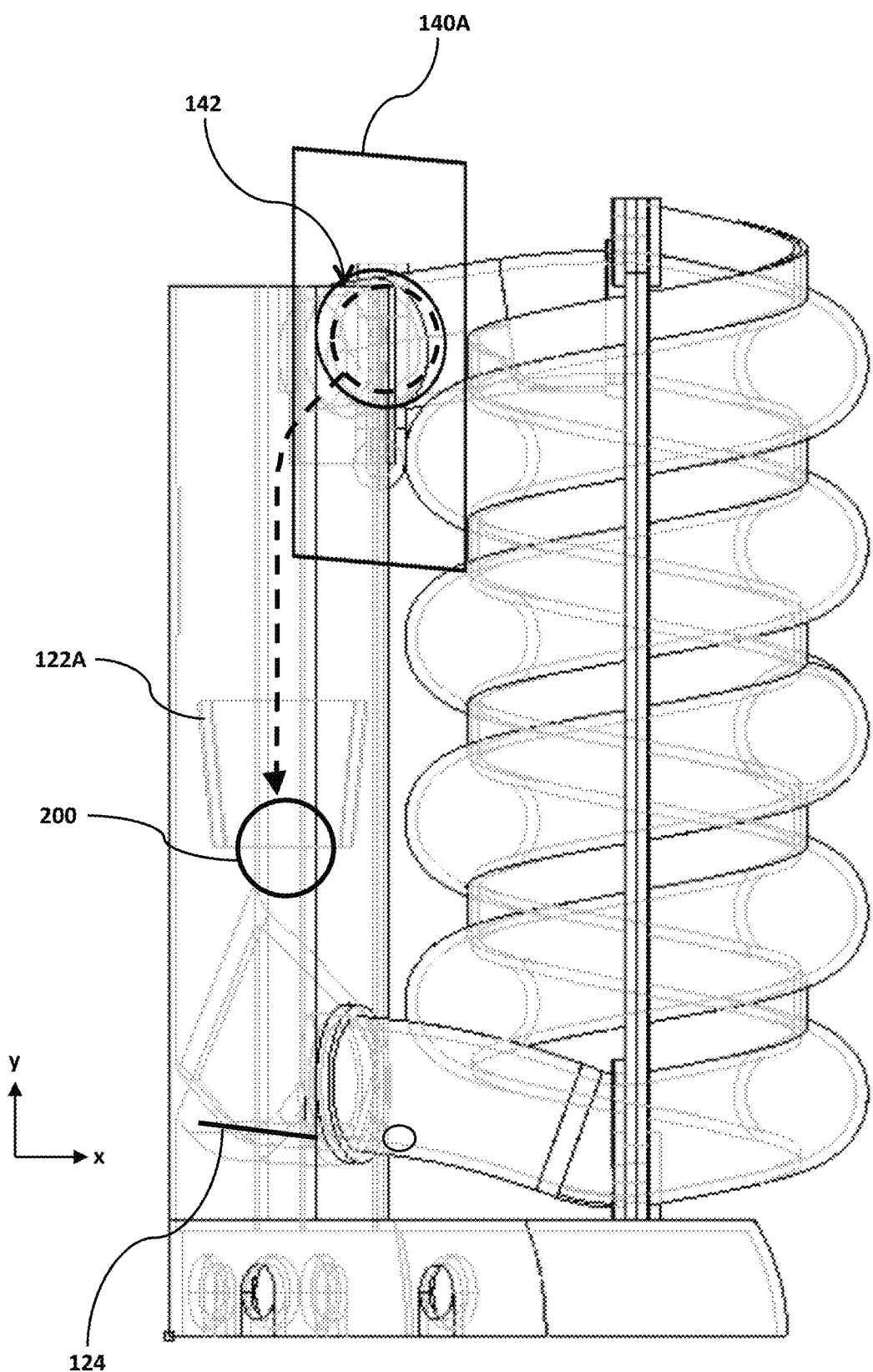
Figure 12:
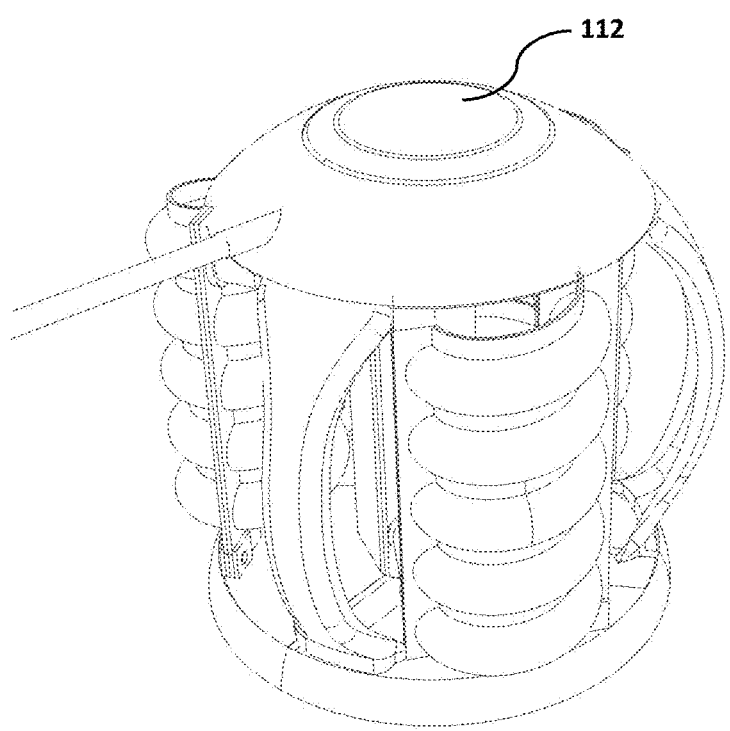
Figure 13:
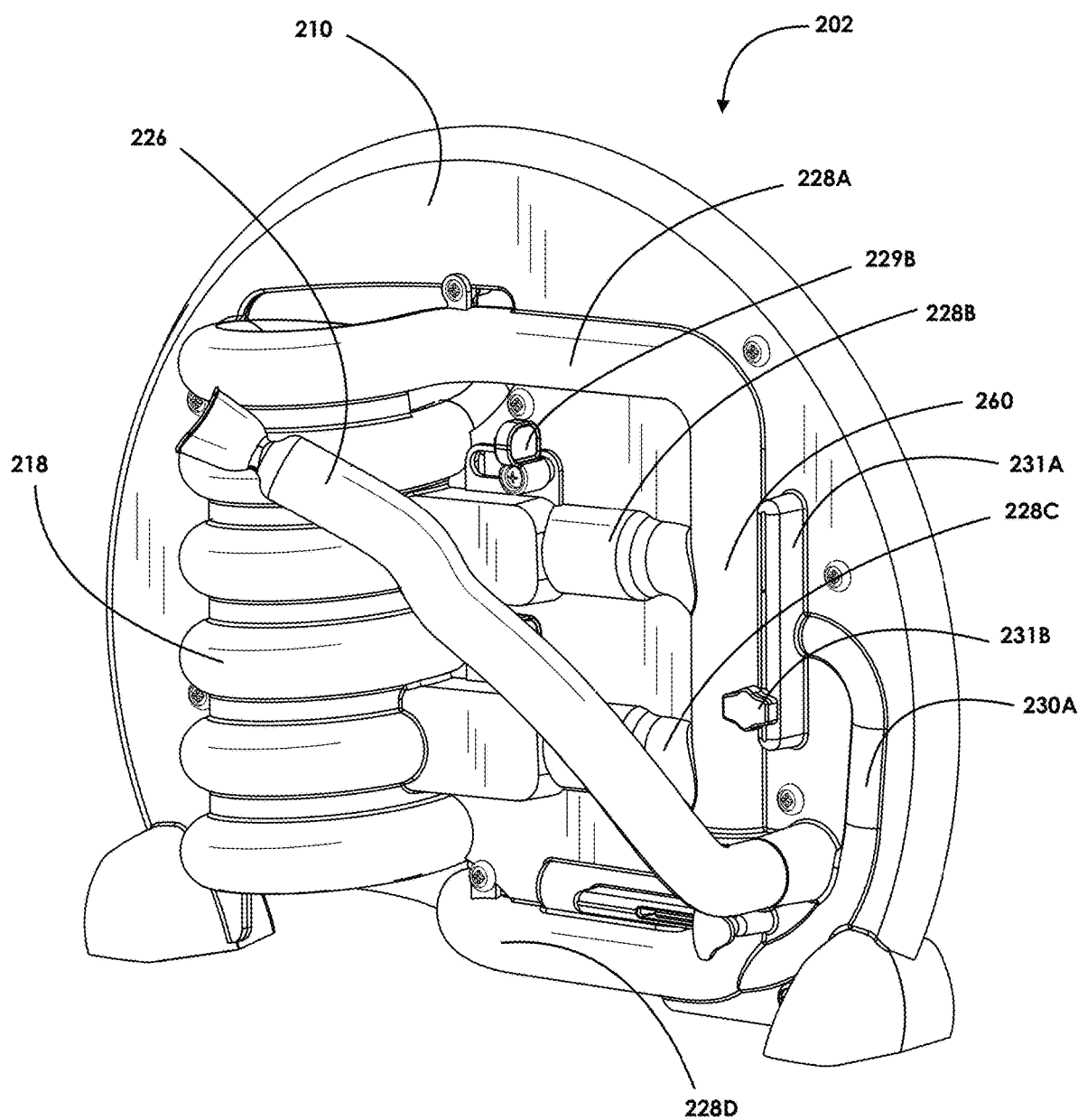
FIG. 13 illustrates another non-limiting exemplary embodiment of the incentive spirometer of the disclosure described herein.
Figure 14:
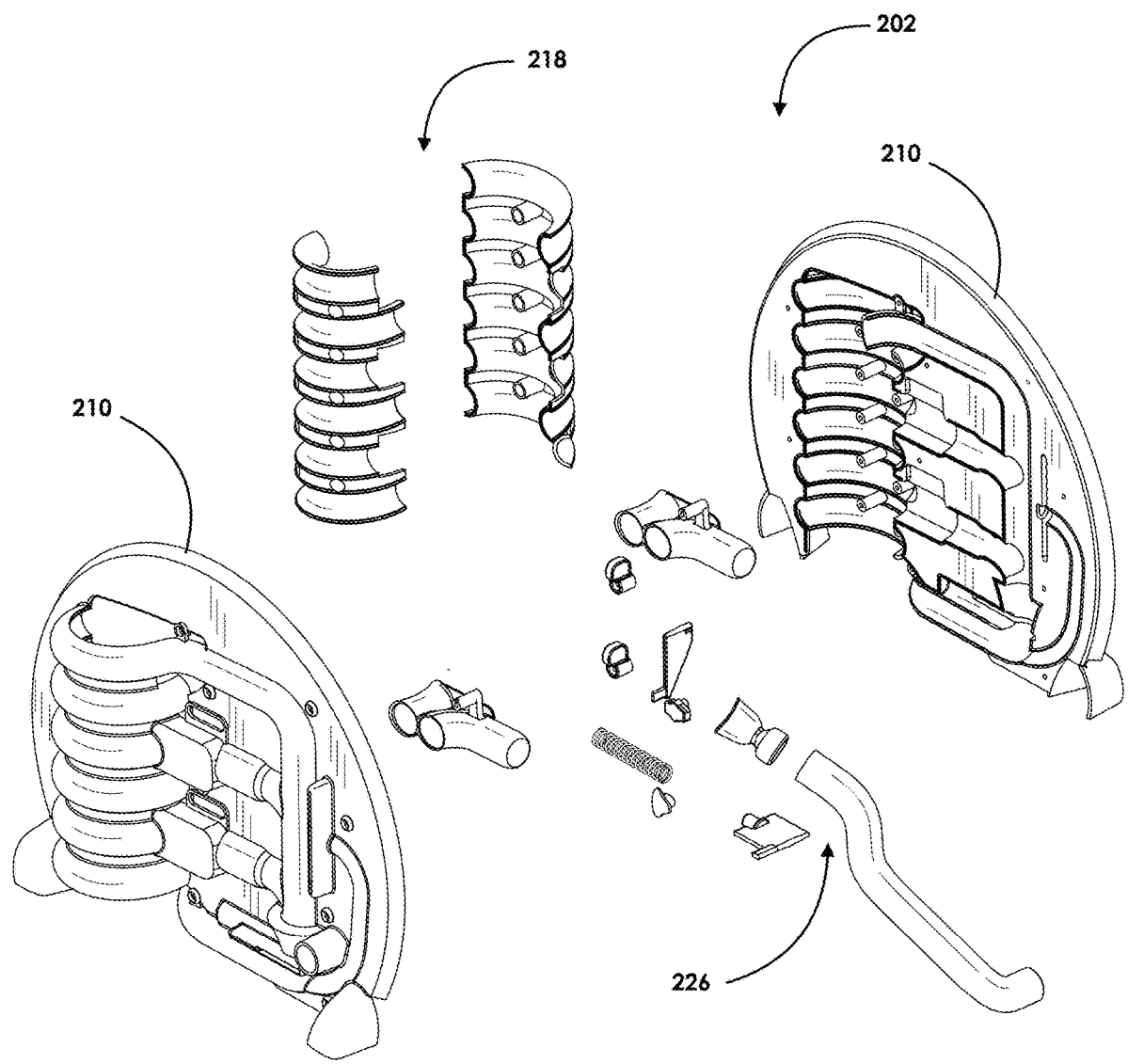
FIG. 14 illustrates an exploded view for the incentive spirometer of FIG. 13.

Referring to FIGS. 7, 8A, and 8B illustrates a perspective sectional view of one-third of the spirometer 100 and FIGS. 9A and 9B illustrate a cross sectional close up side view of one third of the spirometer 100. Here, It is contemplated within the scope of the disclosure described herein that each of chambers 160B, 160C, and tubes 118B, 118C include identical internal and exterior components or substantially identical interior or exterior components as described herein with respect to chamber 160A and tube 118A. Tube 118A, which couples to a downward sloped tubular connector part 118AC (FIG. 8A, 10), further includes an air hole 150 on the bottom surface of part 118AC of tube 118A located near inlet 128. In other embodiments, connector part 118AC and tube 118A can be one unitary piece. In addition, tubes 118B and 118C further include part 118AC; and part 118AC can also be one unitary piece witch each of tubes 118B and 118C. Air hole 150 allows for outside air or atmospheric air to enter the spirometer during the inhalation operation or phase. Here, each of tubes 118A, 118B, and 118C include an air hole 150 in identical or similar locations for (not shown for tubes 118B, 118C) wherein each air hole 150 for tubes 118A, 118B, and 118C can have different sizes, dimensions, or diameters. However, it is contemplated within the scope of the disclosure described herein that their air hole can also be located on the top, or side surfaces of either part 118AC or helical tubes 118A-118C. Specifically, air hole 150 for tube 118A will generally be larger in dimension, diameter, or size than air hole 150 for tube 118B, and air hole 150 for tube 118B will generally be larger in dimension, diameter, or size than air hole 150 for tube 118C. Further, air holes 150 can also be configured as adjustable one-way or two-way valves. In addition, air holes 150 are not limited to a circular or oval configuration, but can be of any shape, polygon, configuration, or dimension. Here, the size of air holes 150 for each of tubes 118A-118C can control the maximal tidal volumes for each of tubes 118A-118C. For example, smaller air holes would mean higher tidal volumes, greater inhalation effort by the user, and slower inhalation speed as opposed to larger air holes 150. In one embodiment, the inspiration speed to complete one operation for all three tubes (i.e. all three balls reaching outlet 130 of tubes 118A-118C) can be approximately 1 second up to and including 15 seconds. Reciprocating release push down button 112 is biased by compression spring 114 disposed within a cylindrical column 172 (FIG. 7, 10) of bezel housing cover 110D, wherein a bottom floor of column 172 supports one end of spring 114. In addition, spring 114 can also have a telescoping rod or one-piece rod disposed within in order to stabilize the spring. Button 112 is further mechanically coupled to gate 140A, which operates to release air pressure within air tube 116 of the spirometer and which further releases ball 200 at outlet 130 of helical tube 118A, thereby allowing the ball which allows it fall through basket 122 within chamber 160A. Specifically gate 140A reciprocates and slides simultaneously with button 112. Here, gate 140A includes apertures 142 that can align with outlet 130 of tube 118A. Specifically, when button 112 is fully depressed (FIG. 12), aperture 142 becomes co-axially aligned with outlet 130. Here, ball 200 (or any first, second, or third balls discussed within the disclosure) can range in size from 0.25 inch in diameter up to and including 1.0 inch in diameter. In addition, the balls can be within an approximate 0.01 inch clearance with respect to an interior wall of either of tubes 118A-118C in order to hug the interior walls of the spiral tubes. In one embodiment, the balls can create an air seal along the interior walls of the tubes 118A-118C as they travel along the length of each tube. For example, the balls can be at least partially or substantially in contact with the interior walls of tubes 118A-118C.

The method of operation for the spirometer will now be described, with reference to FIGS. 1-12. It is contemplated within the scope of the disclosure described herein that the following method can be performed in any sequence or order. Further, not all of the following steps need to be performed for successful inhalation cycle operation of spirometer 100.

1) A first ball 200 (for tube 118A), second ball (not shown) (for tube 118B), and third ball (not shown) (for tube 118C) are each initially disposed or positioned near the lowest point 152 (FIG. 8A) of helical tubes 118A-118C.

2) The user begins his or her breathing exercise or inhalation phase with the spirometer by gradually inhaling air through inhalation tube 126 thereby pressurizing the spirometer, more specifically, pressurizing the tube 116 and tubes 118A-118C.

3) As the user is inhaling via tube 126, negative pressure or low pressure gradually begins to build up within drawtube 126, circular tube 116, and subsequently within helical tubes 118A, 118B, and 118C, creating a suction force or vacuum.

4) This gradual rise of negative or low pressure forces first ball 200 within chamber 160A to be dislodged from its resting place 152 and travel upwards within the helical pattern of tube 118A, where it will then come to a stop at or near outlet 130 (FIG. 7, 9B) and pulled towards the direction of air port 117A. Here, during this inhalation phase, it is important to note that the helical spiral pattern of the spirometer forces the user to perform a steady or sustained inhalation or inspiration operation in order for the user to achieve Sustained Maximal Inspiration (SMI). More specifically, the configuration of tubes 118A-118C prevent the user from "cheating", wherein "cheating" can be defined as the user attempting to quickly or rapidly inhaling through the drawtube and move the ball up the helical tube in quick, rapid burst, un-controlled, un-steady, or un-sustained pattern. In addition, sliding gate 140A (in its un-depressed or un-actuated position) can operate as a stop to prevent ball 200 from going through outlet 130. Here, a tubular connector part 118AB (FIG. 9A-9B, 10), which couples to tube 118A and is part of tube 118A, around outlet 130 can be slightly curved or sloped downward with respect to a horizontal plane near the exit outlet 130, thereby preventing the ball from rolling back down helical tube 118A. More specifically, ball 200 will be held at junction or air port 117A, wherein connector 116A and connector part 118AB of tube 118A intersect. In other embodiments, connector part 118AB and tube 118A can be one unitary piece. In addition, tubes 118B and 118C further include part 118AB and part 118AB can also be one unitary piece witch each of tubes 118B and 118C. Here, the suction force or negative pressure causes ball 200 to move towards air port 117A, wherein the size of the ball is larger than the size of port 117A, and slightly falling within or being positioned or disposed over port 117A, thereby at least partially, substantially or completely sealing air port 117A, and allowing the negative or low pressure to build at second port 116B and spiral tube 118B.

5) Here, as the user continues to inhale, and while ball 200 is still held in place at outlet or near outlet 130 of tube 118A, a second ball (not shown) within chamber 160B begins its travel through helical tube 118B in the same or substantially the same manner and fashion as described with respect to tube 118A. Specifically, the second ball will be held at a second junction or air port 117A (not shown) of connector 116B, thereby sealing its air port and allowing negative pressure to build at port 116C and tube 118C. In addition, gate 140B can also operate as a wall to stop second ball from traveling further past the outlet 130 (not labeled) of tube 118B as it reaches the top of tube 118B around its junction (not shown).

6) As the user continues to inhale, and while first ball 200 and second ball (not shown) and are still held in place at or near their respective outlets, a third ball (not shown) begins its travel through helical tube 118C in the same or substantially same manner and fashion as described with respect to tubes 118A and 118B. Specifically, the third ball will be held at a third junction or air port 117A (not shown) of connector 116B, thereby sealing its port and allowing negative or low pressure to build at port 116C and tube 118C. In addition, gate 140B can also operate as a wall to stop second ball from traveling further past the outlet 130 (not labeled) of tube 118B as it reaches the top of tube 118B around its junction (not shown).

7) While the user is still inhaling or holding his or her inhalation, each ball within each corresponding tubes 118A, 118B, and 118C is held in place at or near their respective outlets 130.

8) At this point, the user can push down on pressure release button 112, which operates to simultaneously push down sliding gates 140A, 140B, and 140C, thereby aligning aperture 142 for each of gates 140A-140C with outlet 130 for each of tubes 118A-118C, thereby simultaneously releasing first, second, and third balls held at or near outlets 130 of each of tubes 118A-118C.

Figure 6:
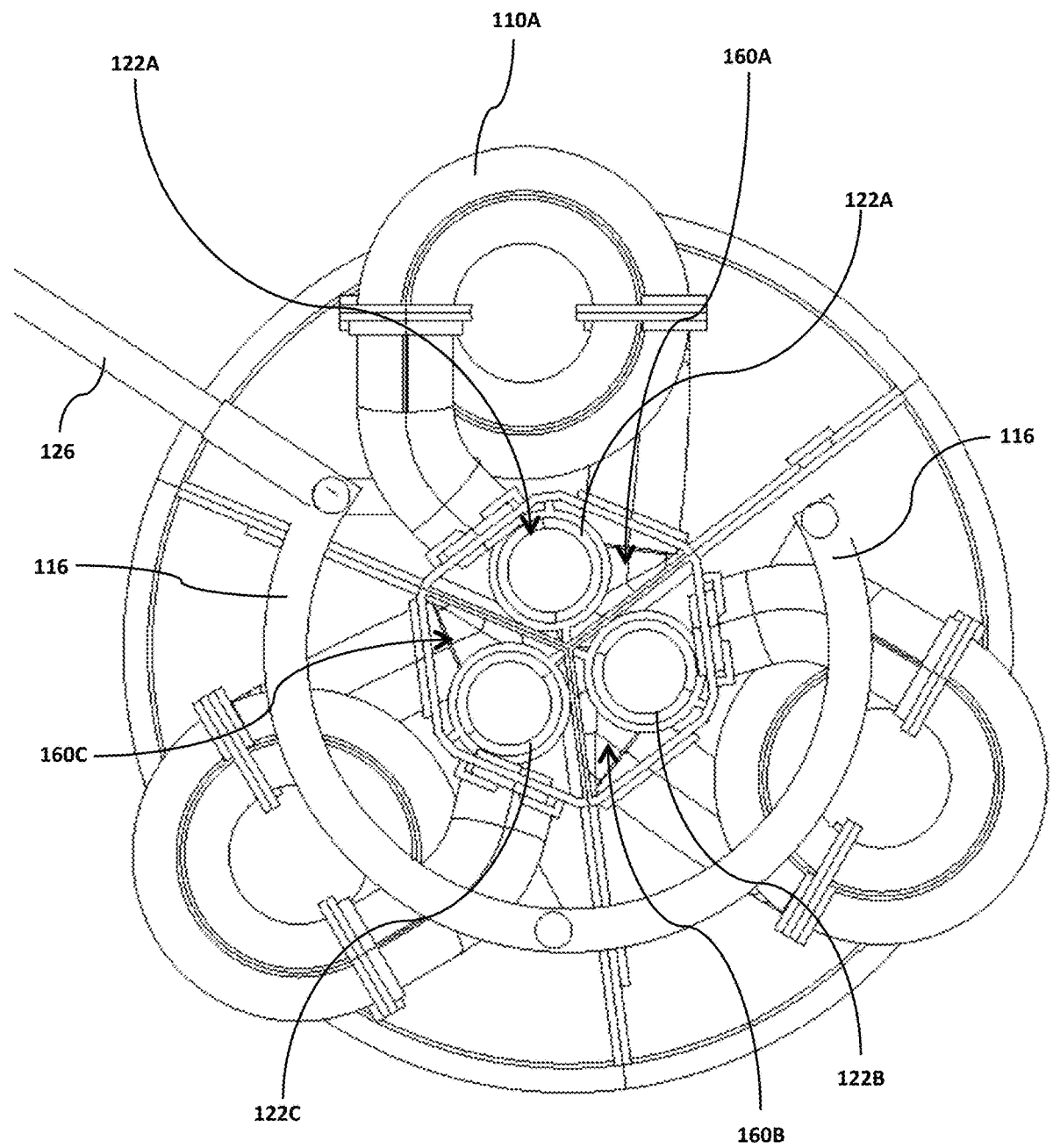
FIG. 6 illustrates a top view of the incentive spirometer with the top bezel and push down button removed.

9) As the balls are released at their corresponding outlets, they subsequently fall downward and through their respective baskets 122A, 122B, and 122C, thereby completing the exercise (FIGS. 6, 8B).

After the balls have fallen through their respective baskets they fall on the surface of the bottom floor 124 within each of their respective chambers 160A, 160B, and 160C, wherein the balls are then guided via the ramp-like configuration of floor 124 towards the inlet of each helical tube to their starting position (FIGS. 8A-8B). At this stage, the aforementioned method can be cycled through as many times as required or recommended for the user.

The aforementioned method of operation assumes that the user has achieved maximum lung capacity. Here, potential tidal volume ranges for spirometer can range from a minimum of 750 ml (250 ml per spiral tube), up to a maximum of 5250 ml (1750 ml per spiral tube). In addition, it is contemplated within the scope of the disclosure described herein that each of spiral tubes 118A-118C can be labeled with indicia such as a scale, markings, barometer, or graphic visual indicator indicating tidal volumes per each spiral tube 118A-118C. Here, the indicia can be along the length of each tube 118A-118C on their exterior surface. For example, tube 118A can be labeled with 250 mL, tube 118B labeled with 500 ml, and tube 118C labeled with 750 ml, or any other configuration depending on the patient or intended manufactured design. In most instances, the user may have to gradually and progressively improve their lung muscles and lung capacity through repetitive use of the spirometer in order to fully complete steps 1) through 8) to achieve maximum tidal volumes. Here, spirometer 100 does not require the user to complete steps 1) through 9) in one sitting but has the option to complete either of steps 1)-3), 1)-4), 1)-5), 1)-6), 1)-7), or 1)-9). Spirometer 100 assists the user to gradually build up their lung capacity in a sustained inspiration or inhalation pattern through practice depending on each users needs, requirements, or recommendations. Here, it is important to note that the helical spiral pattern of helical tubes 118A, 118B, and 118C of the spirometer forces the user to perform a steady or sustained inspiration operation or cycle in order for the user to achieve Sustained Maximal Inspiration (SMI). More specifically, the configuration of tubes 118A-118C prevent the user from "cheating", wherein "cheating" can be defined as the user attempting to quickly or rapidly inhale through the drawtube and move the ball up the helical tube in quick, rapid burst, un-controlled, un-steady or un-sustained pattern. This gradual build up is achieved via the visual and playful nature of the incentive spirometer. Here, tubes 118A-118C and their corresponding baskets 122A-122C, respectively, generally represent various levels of lung capacity achieved through the use of the spirometer. For example, when a user first begins using the device he or she may have the lung capacity and lung strength to be able to inhale enough volume to only pull the first ball upwards through the tube 118A and released through outlet 130 and down through corresponding basket 122A. In other instances, the user may only have the lung capacity and strength to be able to just slightly pull the ball upwards through tube 118A and stop the ball midway through tube 118A, before reaching the top of the tube. In other instances, the user may be able to complete ball travel through both tube 118A and tube 118B, but not tube 118C. Many other instances may become apparent to one of ordinary skill in the art. The spirometer of the disclosure described herein accommodates for all types of users with varying types of lung capacity and/or lung and/or or diaphragm strength.

FIGS. 13-18B illustrates another non-limiting exemplary embodiment of the incentive spirometer of the disclosure described herein. Here, incentive spirometer 202 is shown having a housing 210 comprised of two pieces secured together. In addition, housing 210, as assembled, further includes a single helical tube 218. Spirometer 202 further includes an inhalation draw tube 226 in fluid communication with chambers or tubings 228A, 228B, 228C, 228D, 260, and 230A, among others. In addition, air inlet or port 231A includes an elongated opening allowing air to flow therethrough and into tubing 230A via the negative air pressure of draw tube 226. Further, port 231A further includes an adjustable valve 231B that can operate to adjust the size of the opening of port 231A. Specifically, valve 231B can either slide with port 231A or operate as a turn knob to increase or decrease the amount of air that can be drawn through port 231A for the incentive spirometer. For example, valve 231B can regulate the inhalation pressure or inhalation effort required by a user of the incentive spirometer, such as a larger opening for an easier inhalation effort and smaller opening for a more strenuous inhalation effort by the user.

Still referring to FIGS. 13-18B, incentive spirometer 202 further includes tubings or chambers 228A, 228B, 228C, and 228D in fluid communication with each other and helical tube 218. Specifically, chambers 218, 228A, 228B, 228C, and 228D are adapted to provide a ball, spherical object, wheeled, object, or any object to move therethrough, such as ball 300. Further, each chamber 228B includes a gate switch 229B and chamber 228C includes a gate switch 229C. Here, gate switches 229B and 229C are configured to allow or prevent helical tube 218 to be in fluid communication with chambers 228B and 228C. Specifically, a user can place the gate switch 229C in a closed position whereby a plate or gate will close off chamber 228C to tube 218, whereby ball 300 cannot go through chamber 228C and must go further up helical tube 218, via further inhalation by a user. Alternatively, a user can allow chamber 228C to remain open via placing switch 229 in the open position, thereby allowing ball 300 to flow therethrough to main chamber 260. Similarly, if both chambers 228C and 228B are closed via placing gates 229C and 229B in the closed position, then ball 300 must be drawn up the helical tube by the user to the top chamber 228A and ultimately through main chamber 260, which would require more inhalation effort than if the ball where to allowed to move through chamber 228B or 228C.

Figure 15:
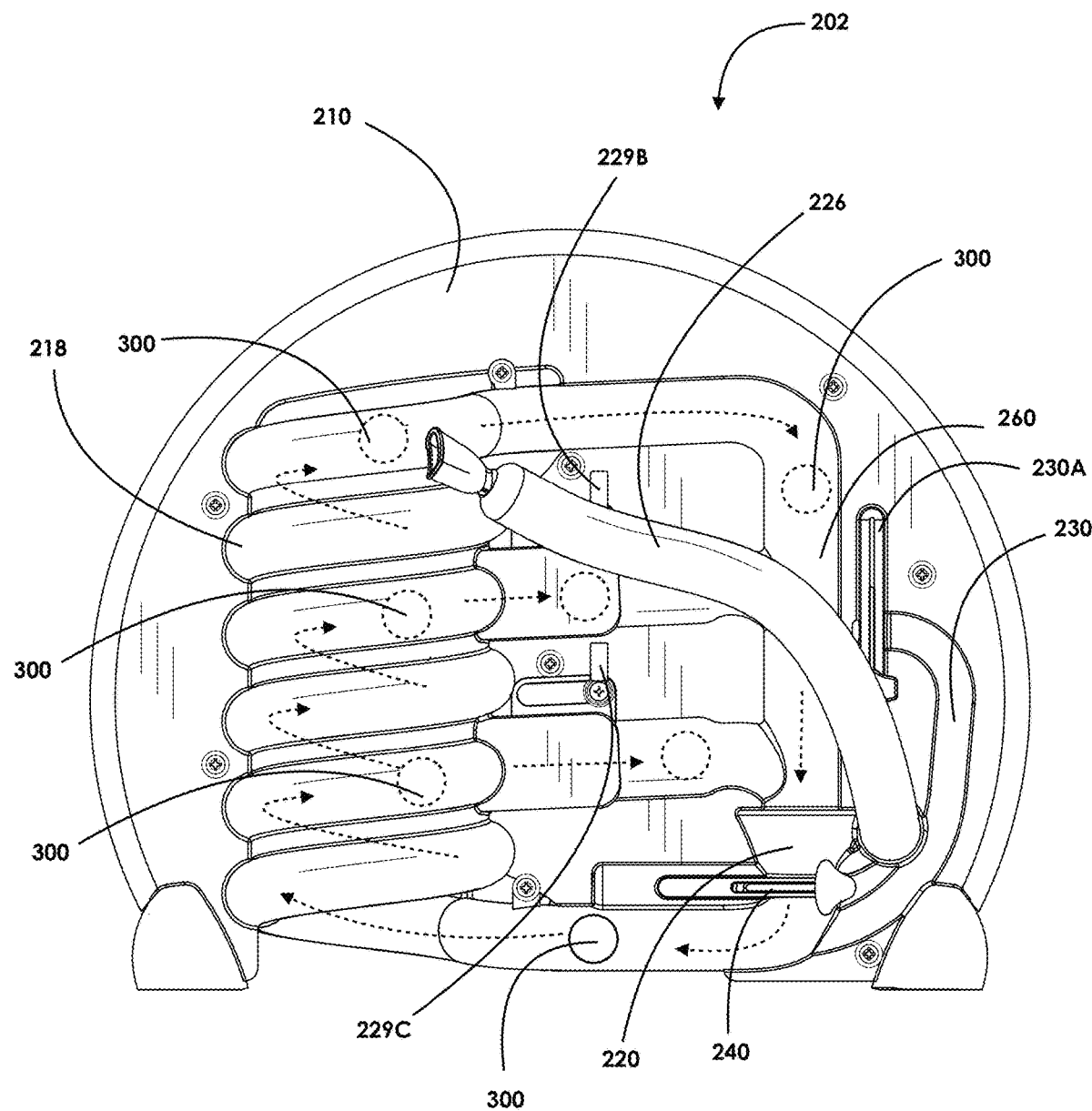
FIG. 15 illustrates a left side view for the incentive spirometer of FIG. 13.
Figure 16:
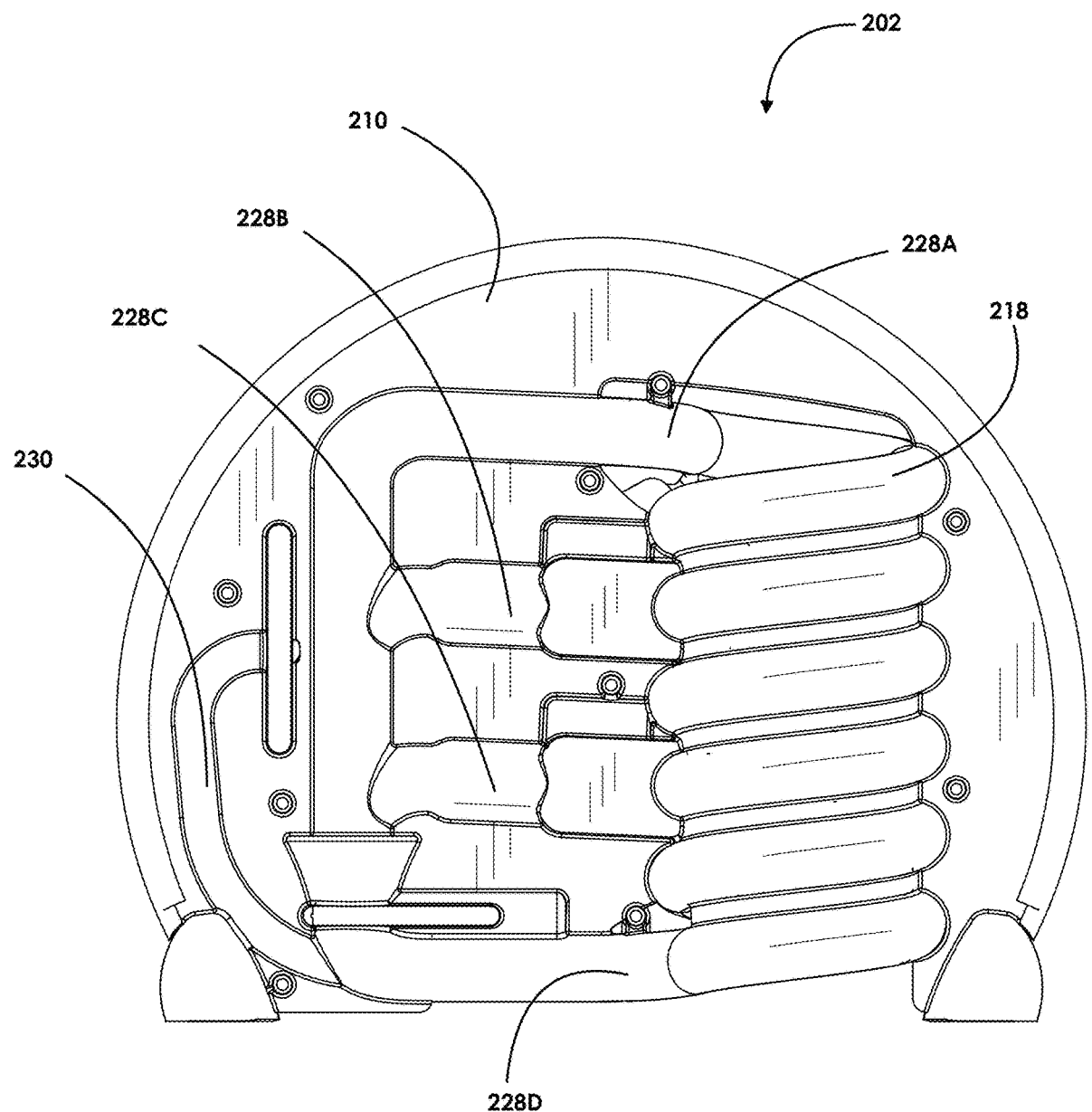
FIG. 16 illustrates a right side view for the incentive spirometer of FIG. 13.
Figure 17A:
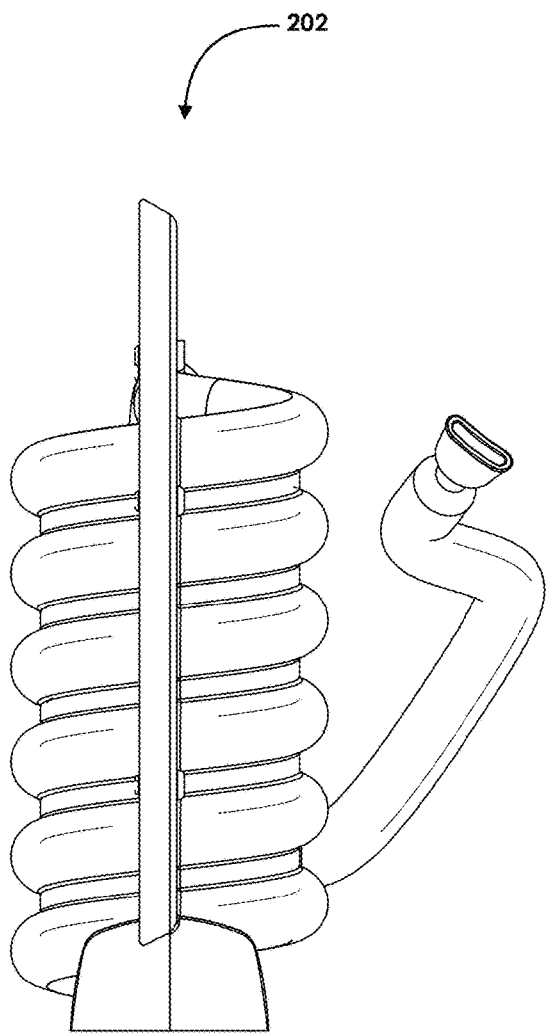
FIG. 17A illustrates a rear side view for the incentive spirometer of FIG. 13.
Figure 17B:
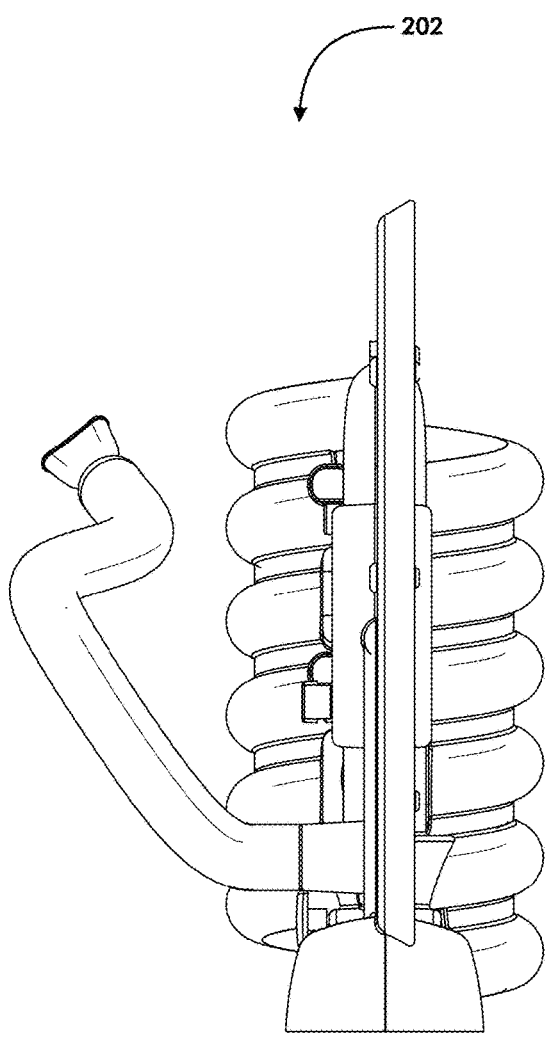
FIG. 17B illustrates front side view for the incentive spirometer of FIG. 13.
Figure 18A:
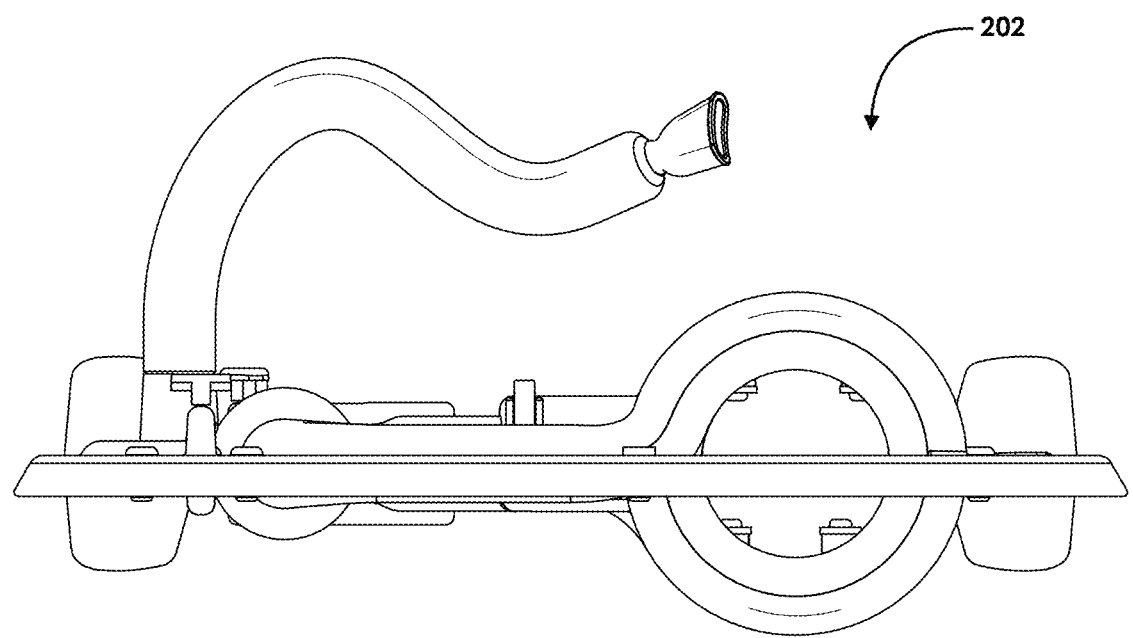
FIG. 18A illustrates a top view for the incentive spirometer of FIG. 13.
Figure 18B:
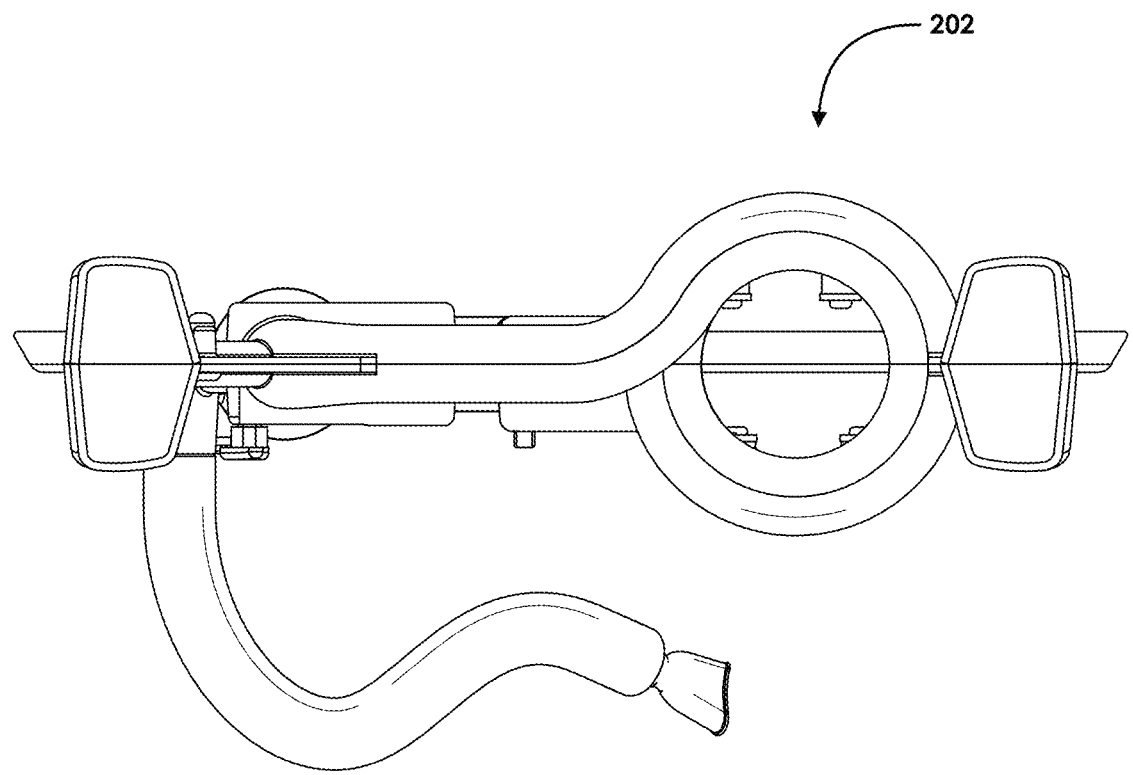
FIG. 18B illustrates a bottom view for the incentive spirometer of FIG. 13.

Still referring to FIGS. 13-18B, incentive spirometer 202 further includes a basket, goal, or opening 220 that allows ball 300 to drop within once it has moved through main chamber 260, after moving through either of chamber 228C, 228B, or 228A. Specifically, once the ball drops within basket 220 then the user has completed one cycle of the inhalation exercise, wherein the basket represents its completion. Spirometer 202 further includes a draw gate 240 that can be engaged or moved laterally to release ball 300 from basket 220, thereby placing the ball in its initial starting position, as shown in FIG. 15. At this stage, the aforementioned method can be cycled through as many times as required or recommended for the user.

It is contemplated within the scope of the disclosure described herein that each chamber 228A, 228B, and 228C of spirometer 202 can represent different levels of achievement or different incentives. For example, if the spirometer 200 is based on a basketball game, then chamber 228A can represent a three-pointer, chamber 228B represent a two-pointer, and chamber 228C representing a layup or one-point. However, it is contemplated within the disclosure described herein that any type of incentive or points system may be assigned to each chamber or level with respect to the helical tube.

The aforementioned method of operation assumes that the user has achieved maximum lung capacity. The potential tidal volume ranges for spirometer 200 can range from a minimum of 250 ml up to a maximum of 5250 ml, among others. In addition, it is contemplated within the scope of the disclosure described herein that each of helical tube 218 and chambers 228A-228C may also be labeled with indicia such as a scale, markings, barometer, or graphic visual indicator indicating tidal volumes per the helical tube. Here, the indicia can be along the length of tube 218, or any of chambers 228A-228C. For example, chamber 228C can be labeled with 250 mL, chamber 228B labeled with 500 ml, and chamber 228A labeled with 750 ml, or any other configuration depending on the patient or intended manufactured design.

In most instances, the user may have to gradually and progressively improve their lung muscles and lung capacity through repetitive use of the spirometer in order to fully complete a cycle to achieve maximum tidal volumes. Spirometer 200 is further configured to assist the user to gradually build up their lung capacity in a sustained inspiration or inhalation pattern through practice depending on each users needs, requirements, or recommendations. Here, it is important to note that the helical spiral pattern of helical tube 218 of the spirometer forces the user to perform a steady or sustained inspiration operation or cycle in order for the user to achieve Sustained Maximal Inspiration (SMI). More specifically, the configuration of tube 218 in communication with either of chambers 228A, 228B, and 228C prevent the user from "cheating", wherein "cheating" can be defined as the user attempting to quickly or rapidly inhale through the drawtube and move the ball up the helical tube in quick, rapid burst, un-controlled, un-steady or un-sustained pattern. Here, this gradual build up is achieved via the visual and playful nature of the incentive spirometer. Here, tube 218 and chambers 228A-228C generally represent various levels of lung capacity achieved through the use of the spirometer. For example, when a user first begins using the device he or she may have the lung capacity and lung strength to be able to inhale enough volume to only pull the first ball upwards through chamber 228C and released through main chamber 260 and down through corresponding basket 220. In other instances, the user may only have the lung capacity and strength to be able to just slightly pull the ball upwards through tube 218 and stop the ball prior to reaching the opening of chamber 228C. Or alternatively, wherein chambers 228C and 228B are closed, then pulling the ball up but before reaching the top of the tube through chamber 228A and the ball falling back to its starting position without going through main chamber 260. In other instances, the user may be able to complete ball travel through chamber 228A. Many other instances may become apparent to one of ordinary skill in the art. The spirometer of the disclosure described herein accommodates for all types of users with varying types of lung capacity and/or lung and/or or diaphragm strength.

Here, spirometer 100 or 202 and their corresponding frames 110 and 210 can be configured and designed to resemble a traditional basketball. However, it is contemplated within the scope of the disclosure described herein that the spirometer and its shell can take any shape or configuration, such as a cylinder, square, rectilinear, oval, ellipsoid, asymmetrical, or any polygon having three or more sides. In addition, the spirometer can resemble any type of sports ball such as a football, soccer ball, tennis ball, volleyball, or any type of ball having any configuration, texture, color, or pattern. In addition, spirometer or frames 110 or 210 or any corresponding component of spirometer 100 or 202 can be translucent, slightly translucent, tinted, or opaque and made of any suitable material, including plastic, thermoplastics, polymers, polypropylene, polycarbonate derived materials, foams, or metals.

Here, the playful, simple, and visual nature of spirometer 100 or 202 provides not only the crucial mechanical exercise or strengthening via repeated SMI's, but also an incentive or motivation for a user to continue their use of the spirometer by attempting to overcome various thresholds. For example, in one session the user may be able to drop the first ball through the first basket and in subsequent sessions be able to drop the second ball through the second basket and/or third ball through the third basket. Alternatively, each basket can represent "points", wherein the first basket is a first point, the second basket is a point higher than the first point, and the third basket is a point higher than the second point. Further, spirometer may further include means for tallying such points. Here, those means can be a digital counter and a digital video display indicating the accrued points and/or functionality for adding, deducting, and resetting points. In other embodiments, each of the helical tubes can be marked with points along the length of each tube, wherein the points increase as the ball travels further upwards through each tube. Here, the points on the tubes can be marked in conjunction with the basket or independently. In other embodiments, the spirometer may have audio effects, such as rings, alarms, sirens, swish sounds, audience, voices, speech, cheering, clapping, among others, related to the one or more balls falling through the baskets. The spirometer may also have visual effects such as flashing lights, LED's, and other lighting or graphic events related to the one or more balls falling through the baskets. However, it is contemplated within the scope of the disclosure described herein that any type of point system, sports games, or recreational game may be incorporated for the incentive spirometer.

It will be apparent to those skilled in the art that various modifications and variations can be made in the disclosed incentive spirometer. It will also be apparent to those skilled in the art that while the method of operating the incentive spirometer is disclosed with a specific order, that specific order is not required. Other embodiments will be apparent to those skilled in the art from consideration of the specification and practice of the disclosed embodiments herein. For example, any of first, second, or third balls, may also be any type of object not limited to a spherical ball. In addition, in other embodiments, the incentive spirometer can be comprised of only one or two spirals, or four or more spirals operating in a similar fashion as disclosed within this disclosure. It is intended that the specification and examples be considered as exemplary only, with a true scope of the disclosure being indicated by the following claims.

What is claimed is:

1. A spirometer, comprising:
   a helical tube, wherein the helical tube comprises a first inlet, first outlet, second outlet, and third outlet;
   a chamber;
   a first tube disposed between the chamber and the second outlet of the helical tube, wherein the first tube comprises a first gate member disposed therein;
   a second tube disposed between the chamber and the third outlet of the helical tube, wherein the third outlet comprises a second gate member disposes therein;
   wherein the chamber is in fluid communication with the first inlet, first outlet, second outlet, and third outlet of the helical tube and the first and second tubes, and wherein the chamber is in a substantially upright configuration and the first tube and second tube each intersect the chamber; and
   an object disposed within the spirometer, wherein the object is adapted to move through the first inlet of the helical tube and through either the first outlet, second outlet, or third outlet.

2. The spirometer of claim 1, wherein the spirometer further comprises a housing further comprised of a first half and second half secured together.

3. The spirometer of claim 1, further comprising an inhalation draw tube in fluid communication with the chamber and helical tube.

4. The spirometer of claim 1, further comprising an adjustable air valve configured to adjust inhalation pressure within the spirometer.

5. The spirometer of claim 1, further comprising a receiving member configured to receive the object therein.

6. The spirometer of claim 5, wherein the receiving member is disposed within the chamber.

7. The spirometer of claim 6, wherein the receiving member is comprised of a basket.

8. The spirometer of claim 5, further comprising a gate disposed below the receiving member.

9. The spirometer of claim 8, wherein the gate is configured to slide.

10. A spirometer, comprising:
a spiral tube, wherein the spiral tube comprises an inlet, a first outlet, a second outlet, and a third outlet;
a chamber in a substantially upright configuration;
a first tube disposed between the chamber and the second outlet of the helical tube, wherein the first tube comprises a first releasable gate member disposed therein between the second outlet and the chamber, and wherein the first tube intersects the chamber;
a second tube disposed between the chamber and the third outlet of the helical tube, wherein the third outlet comprises a second releasable gate member disposed therein between the third outlet and the chamber, and wherein the second tube intersects the chamber;
the first tube in fluid communication with the inlet via the first releasable gate member and the second tube in fluid communication with the inlet via the second releasable gate member; and
an object disposed within the spirometer, wherein the object is adapted to move through the inlet and through the first, second, or third outlets of the spiral tube.

11. The spirometer of claim 10, wherein the spirometer further comprises a housing further comprised of a first half and second half secured together.

12. The spirometer of claim 10, further comprising an inhalation draw tube in fluid communication with the helical tube.

13. The spirometer of claim 10, further comprising an adjustable air valve configured to adjust inhalation pressure within the spirometer.

14. The spirometer of claim 10, further comprising a receiving member configured to receive the object therein.

15. The spirometer of claim 14, wherein the receiving member is disposed within the chamber.

16. The spirometer of claim 15, wherein the receiving member is comprised of a basket.

17. The spirometer of claim 14, wherein the first and second tubes each comprise a sloped configuration.

18. The spirometer of claim 16, further comprising a draw gate below the basket.

19. A spirometer, comprising:
a helical tube comprised of a helix configuration having three or more pitches of substantially the same dimension, wherein the helical tube comprises a first inlet, first outlet, second outlet, and third outlet;
a chamber in a substantially upright configurating, wherein the chamber is in fluid communication with the first inlet, first outlet, second outlet, and third outlet of the helical tube;
a first tube disposed between the chamber and the second outlet of the helical tube, wherein the first tube comprises a first gate member disposed therein;
a second tube disposed between the chamber and the third outlet of the helical tube, wherein the third outlet comprises a second gate member disposed therein; and
an object disposed within the spirometer, wherein the object is adapted to move through the first inlet of the helical tube and through either the first outlet, second outlet and first tube, or third outlet and second tube.

* * * * *